(12) United States Patent
Lorbert et al.

(10) Patent No.: US 8,742,170 B2
(45) Date of Patent: Jun. 3, 2014

(54) PREPARATION OF METHIONINE OR SELENOMETHIONINE FROM HOMOSERINE VIA A 4-SUBSTITUTED 2-AMINOBUTANOIC ACID INTERMEDIATE

(75) Inventors: Stephen J. Lorbert, St. Charles, MO (US); Kevin A. Trankler, St. Charles, MO (US); Richard Vonder Embse, St. Charles, MO (US); Dayna L. Turner, St. Charles, MO (US); Tracy Rode, St. Charles, MO (US); Cynthia K. Snoddy, St. Charles, MO (US); James C. Peterson, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 564 days.

(21) Appl. No.: 13/043,767

(22) Filed: Mar. 9, 2011

(65) Prior Publication Data

US 2011/0224458 A1 Sep. 15, 2011

Related U.S. Application Data

(60) Provisional application No. 61/312,020, filed on Mar. 9, 2010, provisional application No. 61/312,012, filed on Mar. 9, 2010, provisional application No. 61/333,915, filed on May 12, 2010, provisional application No. 61/312,024, filed on Mar. 9, 2010.

(51) Int. Cl.
  *C07C 321/16* (2006.01)
  *C07C 319/14* (2006.01)
  *C07C 391/00* (2006.01)

(52) U.S. Cl.
  USPC .......................................... 562/559; 562/556

(58) Field of Classification Search
  USPC .................................................. 562/559, 556
  See application file for complete search history.

(56) References Cited

U.S. PATENT DOCUMENTS

| | | | |
|---|---|---|---|
| 5,344,767 | A | 9/1994 | Boullais et al. |
| 6,194,616 | B1 | 2/2001 | Spagnol et al. |
| 6,215,024 | B1 | 4/2001 | Choudary et al. |
| 7,368,600 | B2 | 5/2008 | Hateley et al. |
| 7,381,416 | B2 | 6/2008 | Erdelmeir et al. |
| 7,884,240 | B2 | 2/2011 | Hateley et al. |
| 7,906,513 | B2 | 3/2011 | Moore et al. |
| 2003/0083383 | A1* | 5/2003 | Spallholz et al. ............. 514/561 |
| 2005/0101669 | A1* | 5/2005 | Klatt et al. .................... 514/558 |

OTHER PUBLICATIONS

Isaad et al., N-Fmoc Protected w-Azido- and w-Alkynyl-L-amino Acids as Buidling Blocks for the Synthesis of "Clickable" peptides, Eur. J. Org. Chem., 5308-53014, 2008.*
Koch et al., Synthesis of L-(+)-Selenomethionine, Synthesis, 1065-1068, 1993.*
Ates-Alagoz, Synthesis and Antioxidant Activity of New Tetrahydro-Naphthalene-Indole Derivatives as Retinoid and Melatonin Analogs. Arch. Pharm. Chem. Life. Sci. 339, 193-200, 2006.*
Yamamoto et al. An Efficient Oxidation of Long Chain Alkyl Methyl Sulfides to Sulfoxides, Organic Preparations and Procedures International, 32(2), 192-196, 2000.*
Isidro-Llobet, Amino Acid-Protecting Gropus, Chem. Rev., 109, 2455-2404, 2009.*
Zaidlewicz et al., Molecular Addition Compounds. 17. Borane and Chloroborane Adducts with Organic Sulfides for Hydroboration, J. Org. Chem. 65, 6697-6702, 2000.*
Bhanage et al., "Non-Catalytic clean synthesis route using urea to cyclic urea and cyclic urethane compounds", Green Chemistry, 2004, pp. 78-80, vol. 6.
Jagtap et al. "Heterogenous base catalyzed synthesis of 2-oxazolidinones/2-imidiazolidinones via transesterification of ethylene carbonate with beta-aminoalcohols/1,2-diamines", Applied Catalysis A: General; 2008, pp. 133-138, vol. 341, Issues 1-2.
Karnbrock et al., "A New Efficient Synthesis of Acetyltelluro- and Acetylselenomethionine and Their Use in the Biosynthesis of Heavy-Atom Protein Analogs", Journal of the American Chemical Society, 1996, pp. 913-914, vol. 118, No. 4.
Montalbetti et al., "Amide Bond Formation and peptide coupling", Tetrahedron, 2005, pp. 10827-10852, vol. 61, No. 46.
Narender et al., "Liquid phase acylation of amines with acetic acid over HY zeolite", Green Chemistry, 2000, pp. 104-105, vol. 2.
Prasad et al., "Convenient, Cost-Effective, and Mild Method for the N-Acetylation of Anilines and Secondary Amines", Synthetic Communications, 2005, pp. 1189-1185, vol. 35, No. 9.
Foglino et al., "A direct sulfhydrylation pathway is used for methionine biosynthesis in *Pseudomonas aeruginosa*", Microbiology, 1995, pp. 431-439, vol. 141.
International Search Report and Written Opinion from related International Patent Application No. PCT/US11/27641, dated May 16, 2011, 12 pages.
International Search Report and Written Opinion from related International Patent Application No. PCT/US11/27642, dated May 16, 2011, 13 pages.
Mohan et al., "Zeolite catalyzed acylation of alcohols and amines with acetic acid under microwave irradiation", Green Chemistry, 2006, pp. 368-372, vol. 8, Abstract Only.
Office Action from related U.S. Appl. No. 13/043,740, dated Dec. 31, 2012, 7 pages.
Selva et al., "A Simple One-Pot Synthesis of Functionalized Ketimines from Ketones and Amine Hydrochloride Salts", Synthetic Communications: An International Journal for Rapid Communication of Synthetic Organic Chemistry, 1995, pp. 369-378, vol. 25, No. 3, Abstract Only.
Office action dated Dec. 31, 2012 from related U.S. Appl. No. 13/043,740, 7 pgs.

* cited by examiner

*Primary Examiner* — Johann R Richter
*Assistant Examiner* — Mark Luderer
(74) *Attorney, Agent, or Firm* — Polsinelli PC

(57) ABSTRACT

Provided herein are processes for the production of methionine or selenomethionine from homoserine. In particular, the processes proceed via the production of 4-substituted 2-aminobutanoic acid intermediates or derivatives thereof.

28 Claims, No Drawings

PREPARATION OF METHIONINE OR SELENOMETHIONINE FROM HOMOSERINE VIA A 4-SUBSTITUTED 2-AMINOBUTANOIC ACID INTERMEDIATE

CROSS-REFERENCE TO RELATED APPLICATION

This application claims priority to U.S. Provisional Application Ser. No. 61/312,020 filed on Mar. 9, 2010; U.S. Provisional Application Ser. No. 61/312,024 filed on Mar. 9, 2010; U.S. Provisional Application Ser. No. 61/312,012 filed on Mar. 9, 2010; and U.S. Provisional Application Ser. No. 61/333,915 filed on May 12, 2010, each of which is hereby incorporated by reference in their entirety.

FIELD OF THE INVENTION

The present invention relates to the synthesis of methionine or selenomethionine from homoserine, wherein the synthesis pathway proceeds via the production of a 4-substituted 2-aminobutanoic intermediate or derivatives thereof.

BACKGROUND OF THE INVENTION

Methionine is utilized in a variety of fields, from pharmaceuticals to health and fitness products to feed supplements. Selenomethionine is also commercially important because it is a natural source of selenium. Methionine is produced industrially in large amounts; it is currently produced by a completely synthetic pathway that utilizes petroleum-based chemicals and hazardous chemicals. Because of price increases in petroleum, the high costs associated with hazardous waste management, as well as for safety and environmental reasons, there exists a need for alternate methionine synthesis pathways.

SUMMARY OF THE INVENTION

One aspect of the disclosure provides a process for the preparation a compound comprising Formula (III) or a pharmaceutically acceptable salt thereof from a compound comprising Formula (I). The process comprises contacting the compound comprising Formula (I) with a compound comprising X and a proton donor to form a compound comprising Formula (II), wherein the compound comprising X and the proton donor are different compounds. The process further comprises contacting the compound comprising Formula (II) with a compound comprising MeZ to form the compound comprising Formula (III) or the pharmaceutically acceptable salt thereof:

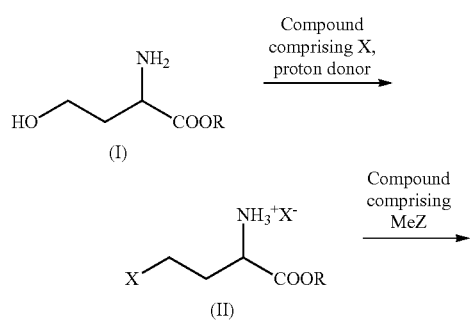

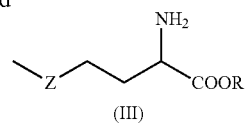

wherein:
the compound comprising MeZ is chosen from an alkali metal methanethiolate, an alkali metal methaneselenoate, and methyl selenol;
Me is methyl;
R is chosen from hydrogen, hydrocarbyl, and substituted hydrocarbyl;
X is an anion chosen from halogen, mesylate, tosylate, brosylate, and nosylate; and
Z is sulfur or selenium Another aspect of the disclosure encompasses a process for preparing a compound comprising Formula (III) or a pharmaceutically acceptable salt thereof from a compound comprising Formula (I). The process comprises contacting the compound comprising Formula (I) with i) a compound comprising X and a proton donor and ii) an acyl donor comprising R' to form a compound comprising Formula (IIa), wherein the compound comprising X and the proton donor are different compounds. The process further comprises contacting the compound comprising Formula (IIa) with a compound comprising MeZ to form a compound comprising Formula (IIIa) or a pharmaceutically acceptable salt thereof. The process further comprises contacting the compound comprising Formula (IIIa) or the pharmaceutically acceptable salt thereof with a deacylating agent to form the compound comprising Formula (III) or the pharmaceutically acceptable salt thereof:

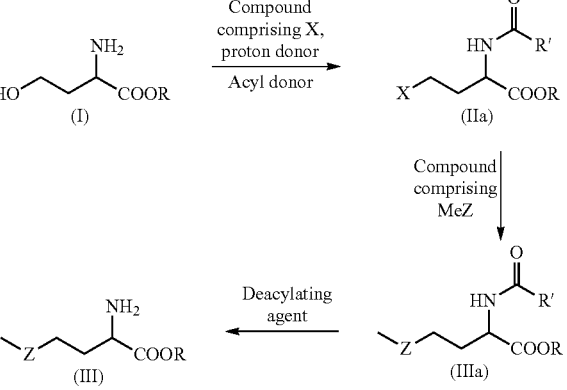

wherein:
the compound comprising MeZ is chosen from an alkali metal methanethiolate, an alkali metal methaneselenoate, and methyl selenol;
Me is methyl;
R is chosen from hydrogen, hydrocarbyl, and substituted hydrocarbyl;
R' is chosen from hydrogen, hydrocarbyl, and substituted hydrocarbyl;
X is an anion chosen from halogen, mesylate, tosylate, brosylate, and nosylate; and
Z is sulfur or selenium.

A further aspect of the disclosure provides a process for the preparation of a compound comprising Formula (V) from a compound comprising Formula (I). The process comprises contacting the compound comprising Formula (I) with a compound comprising X and a proton donor to form a compound comprising Formula (II), wherein the compound comprising X and the proton donor are different compounds. The process further comprises contacting the compound comprising Formula (II) with sodium sulfide and sulfur to form a compound comprising Formula (IV). The last step of the process comprises contacting the compound comprising Formula (IV) with a methylating agent and a proton acceptor to form the compound comprising Formula (V):

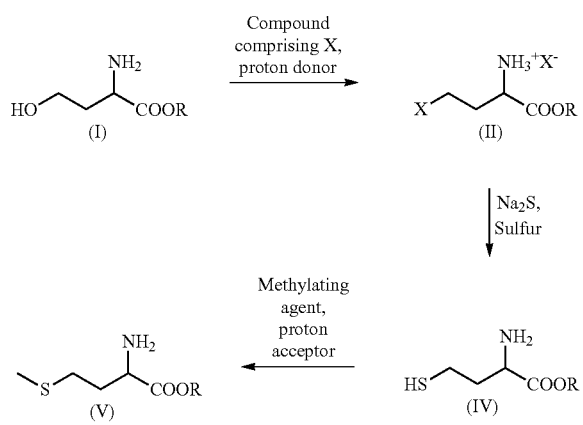

wherein:

R is chosen from hydrogen, hydrocarbyl, and substituted hydrocarbyl; and

X is an anion chosen from halogen, mesylate, tosylate, brosylate, and nosylate.

Still another aspect of the disclosure encompasses a process for preparing a compound comprising Formula (V) from a compound comprising Formula (I). The process comprises contacting the compound comprising Formula (I) with i) a compound comprising X and a proton donor and ii) an acyl donor comprising R' to form a compound comprising Formula (IIa), wherein the compound comprising X and the proton donor are different compounds. The process further comprises contacting the compound comprising Formula (IIa) with sodium sulfide and sulfur to form a compound comprising Formula (IVa). In the next step of the process, the compound comprising Formula (IVa) is contacted with a methylating agent and a proton acceptor to form the compound comprising Formula (Va). The last step of the process comprises contacting the compound comprising Formula (IVa) with a deacylating agent to form the compound comprising Formula (V):

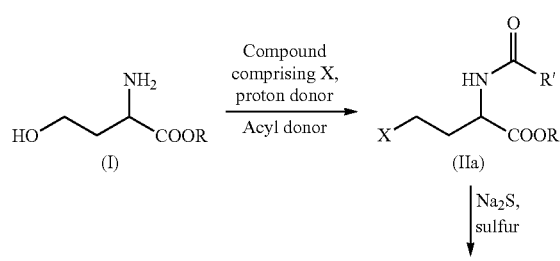

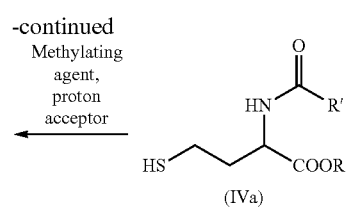

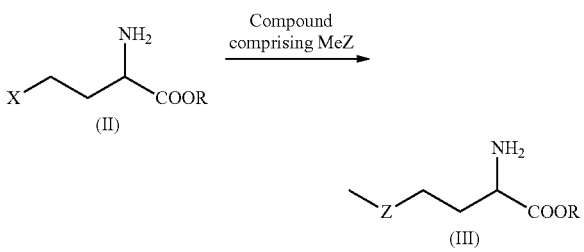

wherein:

R is chosen from hydrogen, hydrocarbyl, and substituted hydrocarbyl;

R is chosen from hydrogen, hydrocarbyl, and substituted hydrocarbyl; and

X is an anion chosen from halogen, mesylate, tosylate, brosylate, and nosylate.

Still another aspect of the disclosure provides a process for preparing a compound comprising Formula (III) or a pharmaceutically acceptable salt thereof from a compound comprising Formula (II) or a pharmaceutically acceptable salt thereof. The process comprises contacting the compound comprising Formula (II) or the pharmaceutically acceptable salt thereof with a compound comprising MeZ to form the compound comprising Formula (III) or the pharmaceutically acceptable salt thereof:

wherein:

the compound comprising MeZ is chosen from an alkali metal methanethiolate, an alkali metal methaneselenoate, and methyl selenol;

Me is methyl;

R is chosen from hydrogen, hydrocarbyl, and substituted hydrocarbyl;

X is a leaving group; and

Z is sulfur or selenium.

A further aspect of the disclosure encompasses of process for preparing a process for preparing a compound Formula (III) or a pharmaceutically acceptable salt thereof from a compound comprising Formula (IIa). The process comprises contacting a compound comprising Formula (IIa) with a compound comprising MeZ to form a compound comprising Formula (IIIa) or a pharmaceutically acceptable salt thereof. The process further comprises contacting the compound comprising Formula (IIIa) or the pharmaceutically acceptable salt thereof with a deacylating agent to form the compound comprising Formula (III) or the pharmaceutically acceptable salt thereof:

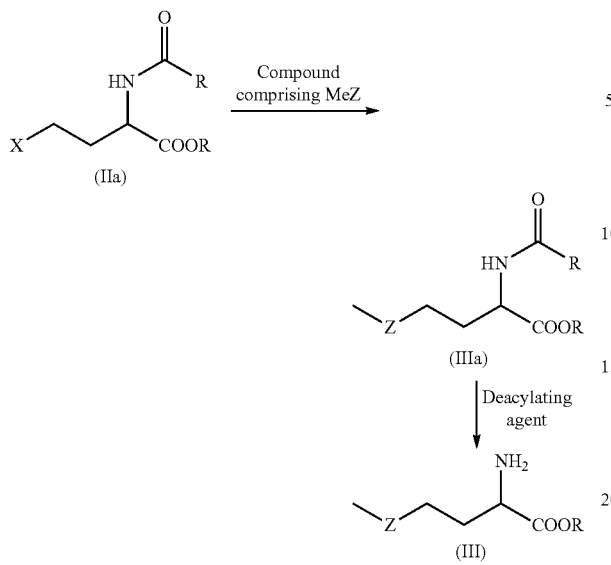

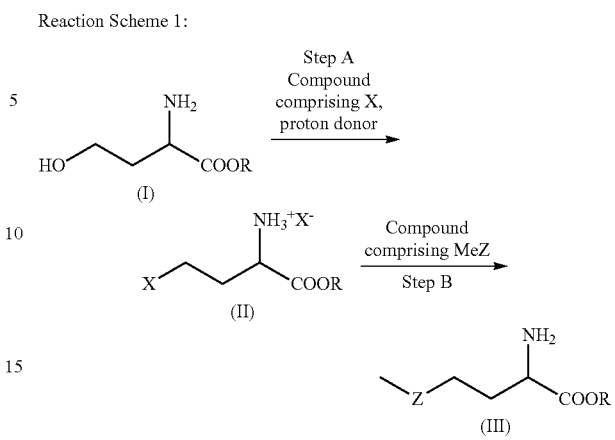

Reaction Scheme 1:

wherein:
- the compound comprising MeZ is chosen from an alkali metal methanethiolate, an alkali metal methaneselenoate, and methyl selenol;
- Me is methyl;
- R is chosen from hydrogen, hydrocarbyl, and substituted hydrocarbyl;
- X is a leaving group; and
- Z is sulfur or selenium.

Other aspects and features of the invention are described in more detail below.

DETAILED DESCRIPTION

The present invention provides processes for the preparation of methionine or selenomethionine, i.e., a compound comprising Formula (III), from homoserine, i.e., a compound comprising Formula (I). In particular, methionine or selenomethionine may be prepared via pathways comprising 4-substituted 2-aminobutanoic acid intermediates or derivatives thereof. These synthetic processes not only avoid the use of hazardous chemicals, but also utilize homoserine, which can be prepared using fermentation processes.

(I) Preparation of a Compound Comprising Formula (III) or a Salt Thereof Via a 4-Substituted 2-Aminobutanoic Intermediate Disclosed herein is a process for preparing a compound comprising Formula (III) or a salt thereof from a compound comprising Formula (I). The process comprises Step A in which the compound comprising Formula (I) is contacted with a compound comprising X and a proton donor, which are different compounds, to form a salt of a compound comprising Formula (II). The process further comprises Step B in which the salt of the compound comprising Formula (II) is contacted with a compound comprising MeZ to form the compound comprising Formula (III) or the pharmaceutically acceptable salt thereof. For the purposes of illustration, Reaction Scheme 1 depicts the preparation of the compound comprising Formula (III) according to this aspect of the invention:

wherein:
- Me is methyl;
- R is chosen from hydrogen, hydrocarbyl, and substituted hydrocarbyl;
- X is an anion chosen from halogen, mesylate, tosylate, brosylate, and nosylate; and
- Z is sulfur or selenium.

(a) Step A—Reaction Mix

Step A of the process comprises contacting the compound comprising Formula (I) with a compound comprising X and a proton donor, which are different compounds, to form a salt of a compound comprising Formula (II). The process commences with the formation of a reaction mixture comprising the compound comprising Formula (I), the compound comprising X, and the proton donor.

(i) Compound Comprising Formula (I)

The identity of the compound comprising Formula (I) can and will vary. In some embodiments, R may be hydrogen, alkyl, alkenyl, aryl, substituted alkyl, substituted alkenyl, or substituted aryl. In general, the alkyl or alkenyl may be from C1 to C6. In an exemplary embodiment, R may be hydrogen. When R is hydrogen, therefore, the compound comprising Formula (I) is homoserine and the compound comprising Formula (III) is methionine or selenomethionine.

(ii) Compound Comprising X

A variety of compounds comprising X are suitable for use in Step A of the process. In some embodiments, the compound comprising X may be a hydrogen halide, such as HCl, HBr, HF, HI, and so forth. In other embodiments, the compound comprising X may be a phosphorous halide such as $PCl_5$, $PCl_3$, $POCl_3$, $PBr_3$, $PF_3$, $PI_3$, and the like. In further embodiments, the compound comprising X may be a boron halide, such as $BCl_3$, $BBr_3$, $BF_3$, $BI_3$, and so forth. In still further embodiments, the compound comprising X may be a thionyl halide, such as $SOCl_2$, $SOBr_2$, $SOF_2$, $SOI_2$, etc. In additional embodiments, the compound comprising X may be p-toluenesulfonic acid or a p-toluenesulfonyl halide. In other embodiments, the compound comprising X may be methanesulfonic acid or a methanesulfonyl halide. In still other embodiments, the compound comprising X may be p-bromobenezenesulfonic acid or a p-bromobenezenesulfonyl halide. In further embodiments, the compound comprising X may be p-nitrobenzene sulfonic acid or a p-nitrobenzene sulfonyl halide. In one embodiment, the compound comprising X may be HCl. In another embodiment, the compound comprising X may be $SOCl_2$.

The amount of the compound comprising X that is contacted with the compound comprising Formula (I) can and will vary. In general, the molar ratio of the compound comprising Formula (I) to the compound comprising X may range from about 1:0.1 to about 1:10. In some embodiments, the molar ratio of the compound comprising Formula (I) to the compound comprising X may range from about 1:0.5 to about 1:5. In certain embodiments, the molar ratio of the compound comprising Formula (I) to the compound comprising X donor may be about 1:0.8, 1:0.9, 1:1, 1:1.1, 1:1.2, 1:1.3, 1:1.4, 1:1.5, 1:1.6, 1:1.7, 1:1.8, 1:1.9, or 1:2.0. In one embodiment, the molar ratio of the compound comprising Formula (I) to the compound comprising X may be about 1:1.

(iii) Proton Donor

The proton donor used in Step A of the process can and will vary. In general, the proton donor has a pKa less than about 0, Suitable proton donors include, without limit, HCl, HBr, HI, HF, $HClO_3$, $HClO_4$, $HBrO_4$, $HIO_3$, $HIO_4$, $HNO_3$, $H_2SO_4$, $MeSO_3H$, $CF_3SO_3H$, and p-toluenesulfonic acid. In one embodiment, the proton donor may be $H_2SO_4$. In another embodiment, the proton donor may be HCl.

The amount of proton donor that is contacted with the compound comprising Formula (I) can and will vary. In general, the molar ratio of the compound comprising Formula (I) to the proton donor may range from about 1:0.001 to about 1:0.1. In some embodiments, the molar ratio of the compound comprising Formula (I) to the proton donor may range from about 1:0.003 to about 1:0.05. In certain embodiments, the molar ratio of the compound comprising Formula (I) to the proton donor may be about 1:0.005, 1:0.008, 1:0.01, 1:0.02, 1:0.03, 1:0.04, or 1:0.05. In one embodiment, the molar ratio of the compound comprising Formula (I) to the proton donor may be about 1:0.01.

(iv) Solvent

The reaction mixture also may comprise a solvent. In general, the solvent will be a protic solvent. Examples of suitable protic solvents include, without limit, water, C1-C4 alcohols, diols such as propylene glycol, and mixtures thereof. Examples of suitable C1-C4 alcohols include methanol, ethanol, isopropanol, n-propanol, isobutanol, n-butanol, s-butanol, t-butanol, and the like. In one embodiment, the solvent may water.

The amount of solvent included in the reaction mixture can and will vary. Typically, the molar ratio of the solvent to the compound comprising Formula (I) may range from about 0.1:1 to about 20:1. In some embodiments, the molar ratio of the solvent to the compound comprising Formula (I) may range from about 0.5:1 to about 10:1. In certain embodiments, the molar ratio of the solvent to the compound comprising Formula (I) may be about 0.5:1, 1:1, 1.5:1, 2:1, 2.5:1, 3:1, 3.5:1, 4:1, 4.5:1, 5:1, or 6:1.

(b) Step A—Reaction Conditions

The reaction of Step A is allowed to proceed at a temperature that may range from about 20° C. to about 200° C. In certain embodiments, the temperature of the reaction may be about 50° C., 55° C., 60° C., 65° C., 70° C., 75° C., 80° C., 85° C., 90° C., 95° C., or 100° C. In one embodiment. Step A may be conducted at a temperature of about 70° C.

The pressure of the reaction can and will vary. The reaction may be conducted at a pressure ranging from about 0 psig to about 100 psig. In one embodiment, the pressure of the reaction Step A may be about 80 psig.

In general, the reaction is allowed to proceed for a sufficient period of time until the reaction is substantially complete. For example, the duration of the reaction may range from about several hours to several days. In one embodiment, the reaction of Step A may be allowed to proceed for about 24 hours. The completeness of the reaction may be determined by any method known to one skilled in the art, such as IR, HPLC, or LC-MS. In this context, a "completed reaction" generally means that the reaction mixture contains a significantly diminished amount of the compound comprising Formula (I) and a significantly increased amount of the compound comprising Formula (II) or the salt thereof compared to the amounts of each present at the beginning of the reaction. Typically, the amount of the compound comprising Formula (I) remaining in the reaction mixture may be less than about 3%, less than about 1%, or preferably less than about 0.5%.

Upon completion of the reaction, the reaction mixture may be cooled and the compound comprising Formula (II) or the salt thereof may be isolated by any means familiar to those of skill in the art. Suitable means include concentration, precipitation, filtration, distillation, phase extraction, crystallization, and the like. For example, an alcohol such as methanol may be added to the reaction mixture to cause precipitation of the compound comprising Formula (II) or the salt thereof. The precipitated product may be isolated by convention means, such as, e.g., filtration. The isolated product may be washed and dried, and analyzed by means familiar to those skilled in the art.

The yield of the compound comprising Formula (II) or the salt thereof can and will vary. Typically, the yield of the compound comprising Formula (II) may be at least about 60% w/w. In some embodiments of the invention, the yield of the compound comprising Formula (II) may be at least about 65%, 70%, 75%, 80%, or 85% w/w. In further embodiments, the yield of the compound comprising Formula (II) or the salt thereof may be at least about 90%, 95%, 97%, or 99% w/w.

(c) Step B—Reaction Mix

The process further comprises Step B in which the compound comprising Formula (II) is contacted with a compound comprising MeZ to form the compound comprising Formula (III) or salt thereof. As used herein, the "compound comprising MeZ" refers to a compound capable of donating a methyl sulfur moiety or a methyl selenium moiety to another compound. Non-limiting examples of suitable compounds comprising MeZ include alkali metal methanethiolates, methyl mercaptan, alkali metal methaneselenoates, and methyl selenol. Typically, the alkali metal will be sodium, potassium, or lithium.

(i) Alkali Metal Methanethiolates

In some embodiments, a salt of the compound comprising Formula (III) in which Z is sulfur may be prepared by contacting the compound comprising Formula (II) with an alkali metal methanethiolate (i.e., alkali metal MeS). Suitable alkali metal methanethiolates include sodium methanethiolate, potassium methanethiolate, or lithium methanethiolate. The alkali metal methanethiolate may be purchased from a commercial chemical supply company. Alternatively, the alkali metal methanethiolate may be synthesized prior to use.

Synthesis of Alkali Metal Methanethiolates.

The alkali metal methanethiolate may be synthesized by contacting methyl mercaptan (also called methanethiol) with an alkali metal hydroxide. Suitable alkali metal hydroxides include, but are not limited to, sodium hydroxide, potassium hydroxide, and lithium hydroxide.

The amount of alkali metal hydroxide contacted with methyl mercaptan can and will vary. In general, the molar ratio of methyl mercaptan to alkali metal hydroxide may range from about 1:0.1 to about 1:10. In one embodiment, the molar ratio of methyl mercaptan to alkali metal hydroxide may be about 1:1

Typically, contact with the alkali metal hydroxide is conducted in the presence of a solvent. The solvent may be a protic solvent, an aprotic solvent, an organic solvent, or combinations thereof. Non-limiting examples of suitable protic solvents include water; an alcohol such as methanol, ethanol, isopropanol, n-propanol, isobutanol, n-butanol, s-butanol, t-butanol; a diol such as propylene glycol, and combinations thereof. Examples of suitable aprotic solvent include without limit acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), ethyl formate, ethyl methyl ketone, formamide, hexachloroacetone, hexamethylphosphoramide, ionic liquids, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. Examples of suitable organic solvents include, but are not limited to, alkane and substituted alkane solvents (including cycloalkanes), aromatic hydrocarbons, esters, ethers, ketones, and combinations thereof. Specific organic solvents that may be used include, for example, benzene, chlorobenzene, ethyl acetate, heptane, hexane, isobutylmethylketone, isopropyl acetate, toluene, and combinations thereof.

In one embodiment, the alkali metal methanethiolate may be synthesized by contacting methyl mercaptan with a solution of alkali metal hydroxide comprising DMSO. In another embodiment, methyl mercaptan may be contacted with a solution of alkali metal hydroxide comprising DMSO and toluene. In yet another embodiment, methyl mercaptan may be contacted with a solution of alkali metal hydroxide comprising an alcohol such as n-butanol.

The amount of solvent included in the reaction mix can and will vary. In general, the molar ratio of the solvent to methyl mercaptan may range from about 0.5:1 to about 10:1. In various embodiments, the molar ratio of the solvent to methyl mercaptan may be about 1:1, 2:1, 3:1, 4:1, or 5:1.

The temperature of the reaction may also vary. Typically, the temperature of the reaction will range from about 0° C. to about 40° C. In some embodiments, the temperature of the reaction may be room temperature (i.e., about 22-25° C.). Typically, the reaction will be conducted under nitrogen or argon. Upon completion of the reaction, the resultant water and/or solvent may be removed by azeotropic distillation.

Reaction with Methanethiolate.

Contact between the compound comprising Formula (II) and the alkali metal methanethiolate produces a salt of the compound comprising Formula (III) in which Z is sulfur. Typically, the molar ratio of the compound comprising Formula (II) to the alkali metal methanethiolate may range from about 1:0.5 to about 1:10. In some embodiments, the molar ratio of the compound comprising Formula (II) to the alkali metal methanethiolate may range from about 1:1 to about 1:5. In further embodiments, the molar ratio of the compound comprising Formula (II) to the alkali metal methanethiolate may be about 1:1.2, 1:1.4, 1:1.6, 1:1.8, 1:2.0, 1:2.2, 1:2.4, 1:2.6, 1:2.8, 1:3.0, 1:3.2, 1:3.4, 1:3.6, 1:3.8, or 1:4.0. In one embodiment, the molar ratio of the compound comprising Formula (II) to the alkali metal methanethiolate may be about 1:3.

Reaction of the compound comprising Formula (II) with the alkali metal methanethiolate is generally conducted in the presence of a solvent. The solvent may be an aprotic solvent, a protic solvent, or combinations thereof. Non-limiting examples of suitable aprotic solvent include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), ethyl formate, ethyl methyl ketone, formamide, hexachloroacetone, hexamethylphosphoramide, ionic liquids, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. In particular, the aprotic solvent may be acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, or combinations thereof. Suitable protic solvents that may be used include water, a C1-C4 alcohol, a diol such as propylene glycol, and combinations thereof. In one embodiment, the solvent may be n-butanol.

The molar ratio of the solvent to the compound comprising Formula (II) can and will vary. In general, the molar ratio of the solvent to the compound comprising Formula (II) may range from about 1:1 to about 50:1. In some embodiments, the molar ratio of the solvent to the compound comprising Formula (II) may be about 4:1, 6:1, 8:1, 10:1, 12:1, 15:1, 20:1, or 25:1. In one embodiment, the molar ratio of the solvent to the compound comprising Formula (II) may be about 10:1. In another embodiment, the molar ratio of the solvent to the compound comprising Formula (II) may be about 15:1.

(ii) Methyl Mercaptan

In other embodiments, the compound comprising Formula (II) may be contacted with methyl mercaptan (MeSH) to form the compound comprising Formula (III) in which Z is sulfur. The molar ratio of the compound comprising Formula (II) to methyl mercaptan may range from about 1:10 to about 1:150. In various embodiments, the molar ratio of the compound comprising Formula (II) to methyl mercaptan may be about 1:20, 1:40, 1:60, 1:80, 1:100, 1:120, or 1:140.

Reaction between the compound comprising Formula (II) and methyl mercaptan may be conducted in the presence of a catalyst. In some embodiments, the catalyst may be a proton donor having a pKa of less than 0. Non-limiting examples of proton donors having this characteristic include HCl, HBr, HI, HClO$_3$, HClO$_4$, HBrO$_4$, HIO$_3$, HIO$_4$, HNO$_3$, H$_2$SO$_4$, MeSO$_3$H, CF$_3$SO$_3$H, alkyl sulfonic acids, aryl sulfonic acids, and the like. In other embodiments, the catalyst may be a proton acceptor having a pKa of greater than about 13. Examples of suitable proton acceptors having this characteristic include borate salts (such as, for example, NaBO$_3$), carbonate salts (such as, for example, Na$_2$CO$_3$, K$_2$CO$_3$, Li$_2$CO$_3$, and the like), organic bases (such as, for example, pyridine, triethylamine, diisopropylethylamine, N-methylmorpholine, N,N-dimethylaminopyridine), and mixtures of any of the above.

In general, the molar ratio of the compound comprising Formula (II) to the catalyst may range from about 1:1 to about 1:20. In some embodiments, molar ratio of the compound comprising Formula (II) to the catalyst may be about 1:3, 1:6, or 1:9.

Contact between the compound comprising Formula (II) and methyl mercaptan may be performed in the presence of a solvent. The solvent may be a protic solvent, an aprotic solvent, an organic solvent, or mixtures thereof. Examples of suitable protic and aprotic solvents are listed above in section (I)(c)(i). Suitable organic solvents include, but are not limited to, alkane and substituted alkane solvents (including cycloalkanes), aromatic hydrocarbons, esters, ethers, ketones, and combinations thereof. The molar ratio of the solvent to the compound comprising Formula (II) may range from about 1:1 to about 50:1. In some embodiments, the molar ratio of the solvent to the compound comprising Formula (II) may range from about 5:1 to about 25:1.

(iii) Alkali Metal Methaneselenoate

In still other embodiments, a salt of the compound comprising Formula (III) in which Z is selenium may be prepared by contacting the compound comprising Formula (II) with an alkali metal methaneselenoate (i.e., alkali metal MeSe). Suitable alkali metal methaneselenoates include sodium methaneselenoate, potassium methaneselenoate, or lithium methaneselenoate. As known to those of skill in the art, the alkali metal methaneselenoate may be prepared by a variety of methods. In one embodiment, for example, the alkali metal methaneselenoate may be prepared by contacting selenium metal with methyllithium, methylsodium, or a similar compound. In another embodiment, sodium methaneselenoate may be prepared by contacting sodium metal, sodium hydride, or sodium borohydride with dimethyldiselenide. In a further embodiment, the methaneselenoate may be prepared by contacting selenium metal with a Grignard reagent (i.e., an alkyl- or aryl magnesium halide such as methyl magnesium bromide or methyl magnesium iodide). In an alternate embodiment, the methaneselenoate may be prepared by contacting methyl selenol with a suitable base. Conditions for each of the above listed reactions are well known to those of skill in the art.

In general, the molar ratio of the compound comprising Formula (II) to the alkali metal methaneselenoate may range about 1:0.5 to about 1:10. In some embodiments, the molar ratio of the compound comprising Formula (II) to the alkali metal methaneselenoate may range from about 1:1 to about 1:5. In further embodiments, the molar ratio of the compound comprising Formula (II) to the alkali metal methaneselenoate may be about 1:1.2, 1:1.4, 1:1.6, 1:1.8, 1:2.0, 1:2.2, 1:2.4, 1:2.6, 1:2.8, 1:3.0, 1:3.2, 1:3.4, 1:3.6, 1:3.8, or 1:4.0. In one embodiment, the molar ratio of the compound comprising Formula (II) to the alkali metal methaneselenoate may be about 1:3.

Contact between the compound comprising Formula (II) and the alkali metal methaneselenoate is generally conducted in the presence of a solvent. The solvent may be an aprotic solvent, a protic solvent, or combinations thereof. Examples of suitable aprotic and protic solvents are listed above in section (I)(c)(i). In one embodiment, the solvent may be n-butanol.

The molar ratio of the solvent to the compound comprising Formula (II) can and will vary. In general, the molar ratio of the solvent to the compound comprising Formula (II) may range from about 1:1 to about 50:1. In some embodiments, the molar ratio of the solvent to the compound comprising Formula (II) may be about 4:1, 6:1, 8:1, 10:1, 12:1, 15:1, 20:1, or 25:1. In one embodiment, the molar ratio of the solvent to the compound comprising Formula (II) may be about 10:1. In another embodiment, the molar ratio of the solvent to the compound comprising Formula (II) may be about 15:1.

(iv) Methyl Selenol

In alternate embodiments, the compound comprising Formula (III) in which Z is selenium may be prepared by contacting the compound comprising Formula (II) with methyl selenol (MeSeH). The molar ratio of the compound comprising Formula (II) to methyl selenol may range from about 1:10 to about 1:150. In various embodiments, the molar ratio of the compound comprising Formula (II) to methyl selenol may be about 1:20, 1:40, 1:60, 1:80, 1:100, 1:120, or 1:140.

Reaction between the compound comprising Formula (II) and methyl selenol may be conducted in the presence of a catalyst. In some embodiments, the catalyst may be a proton donor having a pKa of less than 0. Non-limiting examples of proton donors having this characteristic include HCl, HBr, HI, $HClO_3$, $HClO_4$, $HBrO_4$, $HIO_3$, $HIO_4$, $HNO_3$, $H_2SO_4$, $MeSO_3H$, $CF_3SO_3H$, alkyl sulfonic acids, aryl sulfonic acids, and the like. In general, the molar ratio acid of the compound comprising Formula (II) to the catalyst may range from about 1:1 to about 1:20. In some embodiments, molar ratio of the compound comprising Formula (II) to the catalyst may be about 1:3, 1:6, or 1:9.

Contact between the compound comprising Formula (II) and methyl selenol may be performed in the presence of a solvent. The solvent may be a protic solvent, an aprotic solvent, an organic solvent, or mixtures thereof. Examples of suitable solvents are listed above in section (I)(c)(i). The molar ratio of the solvent to the compound comprising Formula (II) may range from about 1:1 to about 50:1. In some embodiments, the molar ratio of the solvent to the compound comprising Formula (II) may range from about 5:1 to about 25:1.

(d) Step B—Reaction Conditions

The reaction of Step B is allowed to proceed at a temperature that may range from about 20° C. to about 200° C. In certain embodiments, the temperature of the reaction may be about 30° C., 40° C., 50° C., 60° C., 70° C., 80° C., 90° C., 100° C., 110° C., or 120° C. In one embodiment, the reaction of Step B is conducted at a temperature of about 50° C. In another embodiment, the reaction of Step B is conducted at a temperature of about 80° C. The reaction may be conducted under ambient pressure, and under an inert atmosphere (e.g., nitrogen or argon).

In general, the reaction is allowed to proceed for a sufficient period of time until the reaction is substantially complete. Typically, the reaction may be allowed to proceed from about 5 minutes to about 10 hours. The reaction may be performed as a continuous process or a non-continuous process. The duration of the reaction may vary as a function of the temperature. For example, a reaction conducted at 50° C. may be allowed to proceed for a period of time ranging from about 5 hr to about 8 hr; whereas a reaction conducted at 80° C. may be allowed to proceed for about 2 hr. The completeness of the reaction may be determined by any method known to one skilled in the art, such as IR, HPLC, or LC-MS. Typically, the amount of the compound comprising Formula (II) remaining in the reaction mixture may be less than about 3%, less than about 1%, or preferably less than about 0.5%.

Upon completion of Step B of the process, the reaction mixture may be cooled and the compound comprising Formula (III) or the salt thereof may be isolated by any means familiar to those of skill in the art. Suitable means include distillation, concentration, precipitation, filtration, phase extraction, crystallization, and the like. For example, the reaction mixture may be distilled to yield a distillate comprising the compound comprising Formula (III) or its salt. The distillate may be treated such that the compound comprising Formula (III) or its salt precipitates. The precipitated product may be isolated, washed, dried, and/or analyzed by means familiar to those skilled in the art.

The process disclosed herein may produce the compound comprising Formula (III) (i.e., a free acid) or a salt of the compound comprising Formula (III). In embodiments in which the compound comprising MeZ is an alkali metal methanethiolate or an alkali metal methaneselenoate, the compound comprising Formula (III) prepared by the process will be a salt. The salt of the compound comprising Formula (III) may be neutralized with a proton donor (e.g., HCl) to the compound comprising Formula (III). In other embodiments in which the compound comprising MeZ is methyl mercaptan or methyl selenol, the compound produced by the process will be a free acid. In such embodiments, the compound comprising Formula (III) may be converted into a salt using means well know to those of skill in the art. The compound comprising Formula (III) may have an L configuration, a D configuration, or mixture thereof.

The yield of the compound comprising Formula (III) or salt thereof can and will vary. Typically, the yield of the compound comprising Formula (III) or its salt may be at least about 60% w/w. In some embodiments, the yield of the compound comprising Formula (III) or the salt may be at least about 65%, 70%, 75%, 80%, or 85% w/w. In further embodiments, the yield of the compound comprising Formula (III) or salt thereof may be at least about 90%, 95%, 97%, or 99% w/w.

(II) Preparation of a Compound Comprising Formula (IV) or a Salt Thereof Via a 4-Substituted-N-Acyl-2-Aminobutanoic Acid Intermediate Another aspect of the disclosure encompasses a process for preparing a compound comprising Formula (III) from a compound comprising Formula (I), in which the process proceeds via a 4-substituted N-acyl-2-aminobutanoic acid intermediate. The process comprises Step A in which the compound comprising Formula (I) is contacted with i) a compound comprising X and a proton donor, which are different compounds, and ii) an acyl donor comprising R' to form a compound comprising Formula (IIa). Step B of the process comprises contacting the compound comprising Formula (IIa) with a compound comprising MeZ to form a compound comprising Formula (IIIa) or a pharmaceutically acceptable salt thereof. The final step of the process, Step C, comprises contacting the compound comprising Formula (IIIa) or its salt with a deacylating agent to form the compound comprising Formula (III) or a pharmaceutically acceptable salt thereof. For illustrative purposes, Reaction Scheme 2 depicts this aspect of the disclosure:

Reaction Scheme 2:

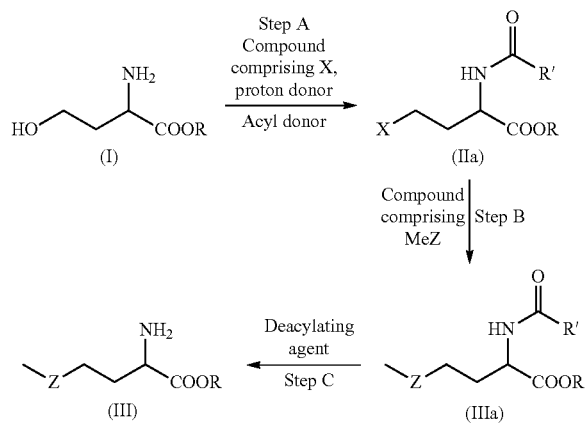

wherein:
Me is methyl;
R is chosen from hydrogen, hydrocarbyl, and substituted hydrocarbyl;
R' is chosen from hydrogen, hydrocarbyl, and substituted hydrocarbyl;

X is an anion chosen from halogen, mesylate, tosylate, brosylate, and nosylate; and
Z is sulfur or selenium.

(a) Step A

Step A of the process comprises contacting the compound comprising Formula (I) with i) a compound comprising X and a proton donor, which are different compounds, and ii) an acyl donor comprising R' to form a compound comprising Formula (IIa). Compounds comprising Formula (I) are detailed above in section (I)(a)(i). Contact with the compound comprising X and the proton donor is detailed above in section (I)(a). Contact with the acyl donor comprising R' is detailed below. In some embodiments, the compound comprising Formula (I) may be contacted with the compound comprising X and the proton donor prior to contact with the acyl donor. In other embodiments, the compound comprising Formula (I) may be contacted with the compound comprising X and the proton donor after contact with the acyl donor. In yet another embodiment, contact with the compound comprising X, the proton donor, and the acyl donor may occur simultaneously.

(i) Acyl Donor

A variety of acyl donors comprising R' are suitable for use in this process. As used herein, an "acyl donor" refers to a compound capable of donating an acyl group to another compound. In general, R' of the acyl donor may be alkyl, alkene, aryl, substituted alkyl, substituted alkene, or substituted aryl. In some embodiments, R' may be methyl, ethyl, or phenyl.

In some embodiments, the acyl donor may be an acyl halide. Non-limiting examples of suitable acyl halides include acetyl chloride, acetyl bromide, propionyl chloride, propionyl bromide, butyryl chloride, butyryl bromide, formyl chloride, formyl fluoride, and so forth. In other embodiments, the acyl donor may be an acid anhydride. Suitable acid anhydrides include, without limit, acetic anhydride, propionic anhydride, and the like.

The amount of acyl donor that is utilized in Step A can and will vary. In general, the molar ratio of the compound comprising Formula (I) to the acyl donor may range from about 1:0.1 to about 1:20. In some embodiments, the molar ratio of the compound comprising Formula (I) to the acyl donor may range from about 1:0.5 to about 1:10. In certain embodiments, the molar ratio of the compound comprising Formula (I) to the acyl donor may be about 1:0.8, 1:0.9, 1:1, 1:1.1, 1:1.2, 1:1.3, 1:1.4, 1:1.5, 1:1.6, 1:1.8, 1:2, 1:3, 1:5, 1:5, 1:6, or 1:7. In one embodiment, the molar ratio of the compound comprising Formula (I) to the acyl donor may be about 1:1.2. In another embodiment, the molar ratio of the compound comprising Formula (I) to the acyl donor may be about 1:1.5.

(ii) Optional Catalyst

Contact with the acyl donor may be conducted in the presence of a catalyst. The catalyst can and will vary depending upon the reactants.

In embodiments in which the acyl donor is an alkyl halide or an acid anhydride, suitable catalysts include, but are not limited to, alkali or earth metal hydroxides, alkali metal alkoxides or aryloxides, alkali or alkaline earth metal amides, secondary amines, tertiary amines, and hindered amines. Non-limiting examples of suitable alkali or alkaline earth metal hydroxides include sodium hydroxide, potassium hydroxide, calcium hydroxide, and the like. Examples of suitable alkali metal alkoxides or aryloxides include, without limit, sodium ethoxide; potassium ethoxide, lithium ethoxide, sodium t-butoxide, potassium t-butoxide, and so forth. Non-limiting examples of suitable alkali or alkaline earth metal amides include sodium amide potassium amide, calcium amide, and the like. Suitable secondary amines include, but are not limited to, dimethylamine, diethylamine, diisopropylamine, and so forth. Non-limiting examples of suitable tertiary amines such as e.g., trimethylamine, triethylamine, and so forth. Suitable hindered amines include, without limit, piperidine, pyrrolidine, and the like. In one embodiment, the catalyst may be a hindered amine such as dimethylaminopyridine.

The amount of optional catalyst included in the reaction mixture can and will vary. In general, the molar ratio of the compound comprising Formula (I) to the catalyst may range from about 1:0.001 to about 1:1. In some embodiments, the molar ratio of the compound comprising Formula (I) to the catalyst may range from about 1:0.005 to about 1:0.5.

Contact with the acyl donor is generally conducted in the presence of a solvent. Suitable solvents are detailed above in section (I)(a)(iv).

Step A of the process may be conducted under conditions detailed above in section (I)(b).

(b) Step B

Step B of the process comprises contacting the compound comprising Formula (IIa) with a compound comprising MeZ to form the compound comprising Formula (IIIa). Suitable reactants and reaction conditions are detailed above in sections (I)(c) and (I)(d).

(c) Step C

The process further comprises Step C in which the compound comprising Formula (IIIa) or its salt is contacted with a deacylating agent to form the compound comprising Formula (III) or salt thereof. In some embodiments, the deacylating agent may be a proton donor. Suitable proton donors, solvents, and ratios of the reactants during Step C of the process are detailed above in section (I)(a)(iii). In other embodiments, the deacylating agent may be an acylase. Treatment of the compound comprising Formula (IIIa) or its salt with an acylase may be performed using methods well known to those of skill in the art.

The reaction of Step C is allowed to proceed at a temperature that may range from about 20° C. to about 100° C. In certain embodiments, the temperature of the reaction may be about 25° C., 30° C., 35° C., 40° C., 45° C., 50° C., 55° C., 60° C., or 65° C. Typically, the reaction is performed at ambient pressure and atmosphere.

In general, the reaction is allowed to proceed for a sufficient period of time until the reaction is substantially complete. For example, the duration of the reaction may range from about 1 hr to about 10 hr. The completeness of the reaction may be determined by any method known to one skilled in the art, such as HPLC or LC-MS. Typically, the amount of the compound comprising Formula (IIIa) remaining in the reaction mixture may be less than about 3%, less than about 1%, or preferably less than about 0.5%.

Upon completion of the reaction, the compound comprising Formula (III) or its salt may be isolated as detailed above in section (I)(d). The compound formed during the process may be a salt or a free acid, which may be inter-converted as detailed above in section (I)(d). The spatial configuration and yield of the compound comprising Formula (III) or its salt are also presented above in section (I)(d).

(III) Preparation of Compound Comprising Formula (V) Via 4-Substituted-2-Aminobutanoic Acid Intermediate A further aspect of the disclosure provides a process for the preparation a compound comprising Formula (V), wherein the process proceeds via 4-substituted 2-aminobutanoic acid and homocysteine intermediates. The process comprises Step A in which a compound comprising Formula (I) is contacted with a compound comprising X and a proton donor to form a compound comprising Formula (II), wherein the compound comprising X and the proton donor are different compounds. The process further comprises Step B in which the compound comprising Formula (II) is contacted with sodium sulfide and sulfur to form a compound comprising Formula (IV). The last step of the process, Step C, comprises contacting the compound comprising Formula (IV) with a methylating agent and a proton acceptor to form the compound comprising Formula (V). Reaction Scheme 3 illustrates this aspect of the disclosure:

Reaction Scheme 3:

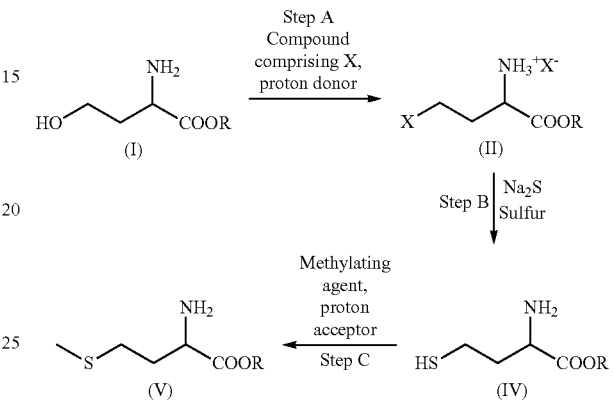

wherein:
R is chosen from hydrogen, hydrocarbyl, and substituted hydrocarbyl; and
X is an anion chosen from halogen, mesylate, tosylate, brosylate, and nosylate.

(a) Step A

Step A of the process comprises contact between the compound comprising Formula (I) with the compound comprising X and the proton donor, wherein the two compounds are different. The reactants and reaction conditions are detailed above in section (I)(a).

(b) Step B—Reaction Mix

The process further comprises Step B in which the compound comprising Formula (II) is contacted with sodium sulfide and sulfur to form the compound comprising Formula (IV). The amount of sodium sulfide and sulfur contacted with the compound comprising Formula (II) can and will vary. For example, the molar ratio of the compound comprising Formula (II) to sodium sulfide may range from about 1:1 to about 1:10. In various embodiments, the molar ratio of the compound comprising Formula (II) to sodium sulfide may be about 1:2. 1:2.3, 1:3. 1:3.3, 1:4, or 1:4.3. Similarly, the molar ratio of the compound comprising Formula (II) to sulfur may range from about 1:1 to about 1:10. In certain embodiments, the molar ratio of the compound comprising Formula (II) to sulfur may be about 1:2. 1:2.3, 1:3. 1:3.3, 1:4, or 1:4.3. In one embodiment, the molar ratio of the compound comprising Formula (II) to sodium sulfide to sulfur may be about 1:3:3.3.

Contact between the compound comprising Formula (II), sodium sulfide, and sulfur is typically conducted in the presence of a solvent. Generally, the solvent may be a protic solvent such as water, formic acid, acetic acid, a C1-C4 alcohol, propylene glycol, and combinations thereof. In one embodiment, the solvent may be methanol. The molar ratio of solvent to the compound comprising Formula (II) may range from about 1:1 to about 1:50. In various embodiments, the molar ratio of the solvent to the compound comprising Formula (II) may be about 4:1, 6:1, 8:1, 10:1, 12:1, 15:1, 20:1, or 25:1. In one embodiment, the molar ratio of the solvent to the compound comprising Formula (II) may be about 10:1.

(c) Step B—Reaction Conditions

The reaction of Step B is allowed to proceed at a temperature that may range from about 20° C. to about 100° C. In certain embodiments, the temperature of the reaction may be about 25° C., 30° C., 35° C., 40° C., 45° C., 50° C., 55° C., or 60° C. In one embodiment, the reaction of Step B is conducted at a temperature of about 40° C.

In some embodiments, contact between the compound comprising Formula (II) and sodium sulfide/sulfur may occur slowly over a period of time. For example, the compound comprising Formula (II) may be mixed with the solvent and heated to the temperature of the reaction. A solution comprising sodium sulfide and sulfur in the solvent may be introduced drop-wise into the solution containing the compound comprising Formula (II). Typically, the reaction mixture is continuously mixed via stirring (or another means) and maintained at the reaction temperature during the period of introduction of the mixture of sodium sulfide/sulfur.

In general, the reaction is allowed to proceed for a sufficient period of time until the reaction is substantially complete. For example, the reaction may be allowed to proceed from about several hours to about 10 hours. The completeness of the reaction may be determined by any method known to one skilled in the art, such as IR, HPLC, or LC-MS. Typically, the amount of the compound comprising Formula (II) remaining in the reaction mixture may be less than about 3%, less than about 1%, or preferably less than about 0.5%.

Upon completion of the reaction of Step B, a solution of sodium borohydride and sodium hydroxide may be added to the reaction mixture. Typically, the solution comprises about 12% sodium borohydride and about 40% sodium hydroxide. The molar ratio of the compound comprising Formula (II) to the sodium borohydride/hydroxide solution may range from about 1:1 to about 1:10. In one embodiment, molar ratio of the compound comprising Formula (II) to the sodium borohydride/hydroxide solution may be about 1:3.3. Those of skill in the art will appreciate that other metal borohydride/hydroxide solutions may be used in this step of the process. The compound comprising Formula (IV) may be isolated by any means familiar to those of skill in the art. Suitable means include distillation, concentration, precipitation, filtration, phase extraction, crystallization, and the like.

The yield of the compound comprising Formula (IV) can and will vary. Typically, the yield of the compound comprising Formula (IV) may be at least about 60% w/w. In some embodiments of the invention, the yield of the compound comprising Formula (IV) may be at least about 65%, 70%, 75%, 80%, or 85% w/w. In further embodiments, the yield of the compound comprising Formula (IV) may be at least about 90%, 95%, 97%, or 99% w/w.

(d) Step C—Reaction Mix

The process further comprises Step C in which the compound comprising Formula (IV) is contacted with a methylating agent and a proton acceptor to form the compound comprising Formula (V).

(i) Methylating Agent

A variety of methylating agents are suitable for use in this step of the process. Non-limiting examples include methyl chloride, methyl iodide, methyl bromide, trimethylphenylammonium chloride, trimethylphenylammonium bromide, trimethylphenylammonium iodide, trimethylphenylammonium sulfate, trimethylphenylammonium methoxide, trimethylphenylammonium ethoxide, trimethyldodecylammonium chloride, trimethyldodecylammonium bromide, trimethyldodecylammonium iodide, tetramethylammonium chloride, tetramethylammonium bromide, tetramethylammonium iodide, dimethyl sulfate, methyl-p-toluenesulfonate, methyl benzenesulfonate, methyl methanesulfonate, methyl trifluoromethansulfonate, dimethyl carbonate, diazomethane, 2,2- dimethyoxypropane, dimethylzinc, iodomethane, methyl fluorosulfonate, trimethy lsilyldiazomethane, and combinations thereof. In one embodiment, the methylating agent may be dimethyl carbonate.

The amount of methylating agent contacted with the compound comprising Formula (IV) can and will vary. Typically, the molar ratio of the compound comprising Formula (IV) to the methylating agent may range from about 1:0.1 to about 1:10. In certain embodiments, the molar ratio of the compound comprising Formula (IV) to the methylating agent may be about 1:0.5, 1:0.75, 1:1, 1:1.25, 1:1.5, 1:1.75, 1:2, 1:2.5, 1:3, or 1:3.5. In one embodiment, molar ratio of the compound comprising Formula (IV) to the methylating agent may be about 1:2.

(ii) Proton Acceptor

The reaction mixture of step C also comprises a proton acceptor. In general, the proton acceptor has a pKa of greater than about 7. Non-limiting examples of suitable proton acceptors having this characteristic include alkali or alkaline earth metal hydroxides such as e.g., sodium hydroxide, potassium hydroxide, calcium hydroxide, and the like; alkali or alkaline earth metal carbonates such as e.g., potassium carbonate, sodium carbonate, lithium carbonate, and so forth; alkali or alkaline earth metal bicarbonates such as e.g., sodium bicarbonate, potassium bicarbonate, and the like; alkali metal alkoxides or aryloxides such as e.g., sodium ethoxide; potassium ethoxide, lithium ethoxide, sodium t-butoxide, potassium t-butoxide, and so forth; alkali metal alkylcarboxylates or arylcarboxylates such as sodium acetate, sodium propionate, and the like; alkali metal phosphates such as e.g., sodium di-basic phosphate, sodium tri-basic phosphate, potassium di-basic phosphate, potassium tri-basic phosphate, and so forth; alkali or alkaline earth metal amides such as e.g., sodium amide potassium amide, calcium amide, and the like; secondary amines such as dimethylamine, diethylamine, diisopropylamine, and so forth; hindered amines such as piperidine, pyrrolidine, and the like; and tertiary amines such as e.g., trimethylamine, triethylamine, and so forth. In exemplary embodiments, the proton acceptor may be sodium ethoxide or sodium hydroxide.

The molar ratio of the compound comprising Formula (IV) to the proton acceptor can and will vary. In general, the molar ratio of the compound comprising Formula (IV) to the proton acceptor will range from about 1:0.1 to about 1:10. In various embodiments, the molar ratio of the compound comprising Formula (IV) to the proton acceptor may be about 1:0.5, 1:0.75, 1:1, 1:1.25, 1:1.5, 1:1.75, 1:2, 1:2.5, 1:3, or 1:3.5. In one embodiment, molar ratio of the compound comprising Formula (IV) to the proton acceptor may be about 1:2.

(iii) Solvent

Step C of the process generally is conducted in the presence of a solvent. Typically, the solvent is a polar solvent. Suitable polar solvents include water, formic acid, acetic acid, a C1-C4 alcohol, propylene glycol, and combinations thereof. The molar ratio of the solvent to the compound comprising Formula (IV) may range from about 0.5:1 to about 20:1. In certain embodiments, molar ratio of the solvent to the compound comprising Formula (IV) may be about 0.2:1, 1:1, 1:1.5, 1:2, 1:2.5, 1:3, 1:3.5, or 1:4.

(e) Step C—Reaction Conditions

The reaction of Step C may be conducted at a temperature from about 20° C. to about 200° C. In certain embodiments, the temperature of the reaction may be about 30° C., 40° C., 50° C., 60° C., 70° C., 80° C., 90° C., 100° C., 110° C., or 120° C. In one embodiment, the temperature of the reaction may be about 65° C. The reaction may be conducted under ambient pressure, and under an inert atmosphere (e.g., nitrogen or argon).

In general, the reaction is allowed to proceed for a sufficient period of time until the reaction is substantially complete. Typically, the reaction may be allowed to proceed from about 1 hour to about 10 hours. The completeness of the reaction may be determined by any method known to one skilled in the art, such as IR, HPLC, or LC-MS. Typically, the amount of the compound comprising Formula (IV) remaining in the reaction mixture may be less than about 3%, less than about 1%, or preferably less than about 0.5%.

Upon completion process, the compound comprising Formula (V) may be isolated by any means familiar to those of skill in the art. Suitable means include distillation, concentration, precipitation, filtration, phase extraction, crystallization, and the like. The precipitated product may be isolated, washed, dried, and/or analyzed by means familiar to those skilled in the art.

The compound comprising Formula (V) may be converted into a pharmaceutically acceptable salt using methods known to those of skill in the art. The compound comprising Formula (V) may have an L configuration, a D configuration, or mixture thereof.

The yield of the compound comprising Formula (V) can and will vary. Typically, the yield of the compound comprising Formula (V) may be at least about 60% w/w. In some embodiments, the yield of the compound comprising Formula (V) may be at least about 65%, 70%, 75%, 80%, or 85% w/w. In further embodiments, the yield of the compound comprising Formula (V) may be at least about 90%, 95%, 97%, or 99% w/w.

(IV) Preparation of a Compound Comprising Formula (V) Via a 4-Substituted-N-Acyl-2-Aminobutanoic Acid Intermediate Still another aspect of the disclosure encompasses a process for the preparation of a compound comprising Formula (V), wherein the process proceeds via 4-substituted-N-acyl-2-aminobutanoic acid and N-acyl homocysteine intermediates. The process comprises Step A in which a compound comprising Formula (I) is contacted with i) a compound comprising X and a proton donor, wherein the compound comprising X and the proton donor are different compounds, and ii) an acyl donor comprising R' to form a compound comprising Formula (IIa). The process further comprises Step B in which the compound comprising Formula (IIa) is contacted with sodium sulfide and sulfur to form a compound comprising Formula (IVa). Step C of the process comprises contacting the compound comprising Formula (IVa) with a methylating agent and a proton acceptor to form the compound comprising Formula (Va). The process further comprises Step D in which the compound comprising Formula (Va) is contacted with a deacylating agent to form the compound comprising Formula (V). For the purposes of illustration, Reaction Scheme 4 depicts this aspect of the disclosure:

Reaction Scheme 4:

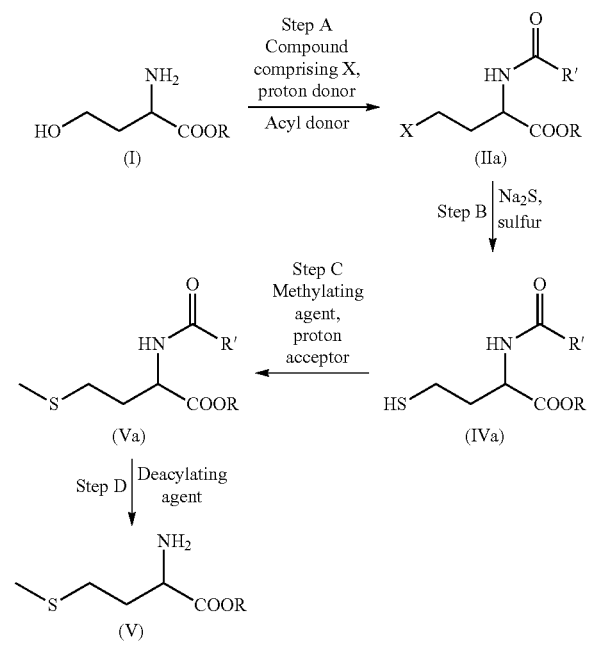

wherein:
R is chosen from hydrogen, hydrocarbyl, and substituted hydrocarbyl;
R' is chosen from hydrogen, hydrocarbyl, and substituted hydrocarbyl; and
X is an anion chosen from halogen, mesylate, tosylate, brosylate, and nosylate.

(a) Step A

The process commences with Step A in which the compound comprising Formula (I) is contacted with i) a compound comprising X and a proton donor and ii) an acyl donor comprising R' to form the compound comprising Formula (IIa), as detailed above in section (II)(a).

(b) Step B

In Step B of the process, the compound comprising Formula (IIa) is contacted with sodium sulfide and sulfur to form the compound comprising Formula (IVa). Contact with sodium sulfide and sulfur is detailed above in sections (III)(b) and (III)(c).

(c) Step C

The process further comprises Step C in which the compound comprising Formula (IVa) is contacted with a methylating agent and a proton acceptor to form the compound comprising Formula (Va). Contact with the methylating agent and the proton acceptor is described above in sections (III)(d) and (III)(e).

(d) Step D

The final step, Step D, of the process comprises contacting the compound comprising Formula (Va) with a deacylating agent to form the compound comprising Formula (V). Contact with the deacylating agent is detailed above in section (II)(c).

(V) Contact Between a 4-Substituted-2-Aminobutanoic Acid and a Compound Comprising MeZ Another aspect of the disclosure encompasses a process in which a compound comprising Formula (II) or salt thereof is contacted with a compound comprising MeZ to prepare the compound comprising Formula (III) or salt thereof. Reaction Scheme 5 depicts this aspect of the disclosure:

Reaction Scheme 5:

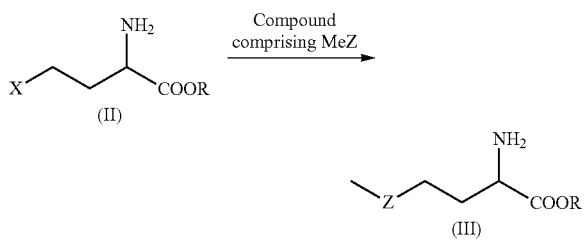

wherein:
Me is methyl;
R is chosen from hydrogen, hydrocarbyl, and substituted hydrocarbyl;
X is a leaving group; and
Z is sulfur or selenium.

The process comprises contacting the compound comprising Formula (II) or its salt with a compound comprising MeZ to form the compound comprising Formula (III) or its salt. Suitable reactants and reaction conditions are described above in sections (I)(c) and (I)(d), respectively.

(VI) Contact Between a 4-Substituted-N-Acyl-2-Aminobutanoic Acid and a Compound Comprising MeZ Yet another aspect of the disclosure provides a process in which a compound comprising Formula (IIa) is contacted with a compound comprising MeZ to from a compound comprising Formula (IIIa) or a salt thereof. The process further comprises contacting the compound comprising Formula (IIIa) or its salt with a deacylating agent to form the compound comprising Formula (III) or salt thereof. Reaction Scheme 6 depicts this aspect of the disclosure:

Reaction Scheme 6:

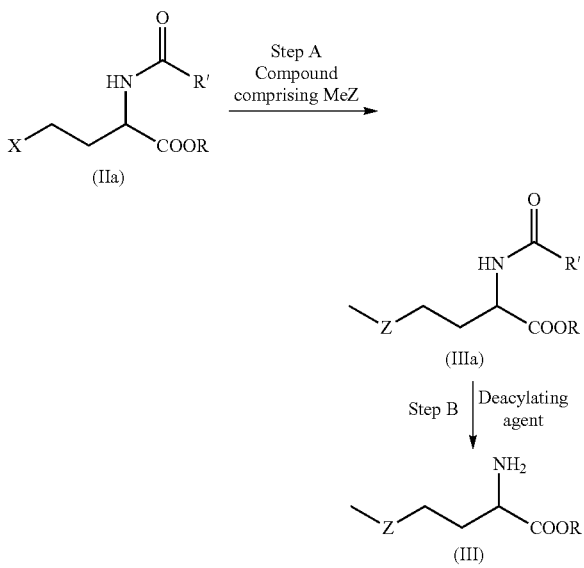

wherein:
Me is methyl;
R is chosen from hydrogen, hydrocarbyl, and substituted hydrocarbyl;
R' is chosen from hydrogen, hydrocarbyl, and substituted hydrocarbyl;
X is a leaving group; and
Z is sulfur or selenium.

The process comprises contacting the compound comprising Formula (IIa) with a compound comprising MeZ to form the compound comprising Formula (IIIa) or a salt thereof. Contact with the compound comprising MeZ is described above in sections (I)(c) and (I)(d).

The process further comprises contact between the compound comprising Formula (IIIa) or its salt with a deacylating agent. Suitable deacylating agents and conditions are detailed above in section (II)(c).

DEFINITIONS

To facilitate understanding of the invention, several terms are defined below.

The term "acyl," as used herein alone or as part of another group, denotes the moiety formed by removal of the hydroxyl group from the group COOH of an organic carboxylic acid, e.g., RC(O), wherein R is $R^1$, $R^1O—$, $R^1R^2N—$, or $R^1S—$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl," "substituted alkyl," "substituted alkenyl," "substituted aryl," and "substituted heteroaryl" moieties described herein are hydrocarbyl, alkyl, alkenyl, aryl, and heteroaryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, keto, acyl, acyloxy, nitro, amino, amido, nitro, cyano, thiol, ketals, acetals, esters, and ethers.

When introducing elements of the present invention or the preferred embodiments(s) thereof, the articles "a", "an", "the" and "said" are intended to mean that there are one or more of the elements. The terms "comprising", "including"

and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

EXAMPLES

The following examples detail various embodiment of the invention.

Example 1

Synthesis of Methionine—Via Sodium Methanethiolate

Approximately 1 equivalent of homoserine, 0.01 equivalent of sulfuric acid may be combined with water in a reactor. The reactor may be sealed and 1.1 equivalent of anhydrous HCl (gas) may be may be added to the reactor. The reaction mixture may be heated to about 70° C. and maintained at about 80 psi for about 24 hours. The reaction mixture may be cooled and about 10 equivalents of methanol may be added, such that the product precipitates. The product (i.e., 4-chloro-2-aminobutanoic acid hydrochloride) may be isolated by filtration.

The 4-chloro-2-aminobutanoic acid HCl may be combined with 10 equivalents of n-butanol in a reactor. To the reactor, may be added 3 equivalents of sodium methanethiolate in n-butanol. The reaction mixture may be heated to about 80° C. for about 2 hr. The solvent may be removed by distillation and water may be added to the product. The aqueous solution comprising the sodium salt of methionine may be washed with methyl isobutyl ketone (MIBK) to remove impurities.

The solution of the sodium salt of methionine may be treated with 37% HCl (1.2 equivalents) and the pH may be adjusted to about 5.7. The resultant solution may be concentrated and methanol may be added to precipitate NaCl, which may be removed by filtration. The filtrate may be cooled, causing the methionine to precipitate. The precipitated methionine may be isolated by filtration and washed with cold water. The mother liquor may be recycled to recover more methionine product.

Example 2

Synthesis of Methionine—Via Sodium Sulfide

Approximately 1 equivalent of homoserine, 0.01 equivalent of sulfuric acid may be combined with water in a reactor. The reactor may be sealed and 1.1 equivalent of anhydrous HCl (gas) may be may be added to the reactor. The reaction mixture may be heated to about 70° C. and maintained at about 80 psi for about 24 hours. The reaction mixture may be cooled and about 10 equivalents of methanol may be added, such that the product precipitates. The product (i.e., 4-chloro-2-aminobutanoic acid hydrochloride) may be isolated by filtration.

The 4-chloro-2-aminobutanoic acid HCl may be combined with 10 equivalents of methanol in a reactor. The mixture may be heated to about 40° C. A solution of 3 equivalents of sodium sulfide and 3.3 equivalents of sulfur in methanol may be added dropwise to the stirring reaction mixture over a period of about 4 hr. The reaction mixture may be stirred at 40° C. for another 3 hr. A solution of 3.3 equivalents of sodium borohydride/NaOH and water may be added to the reaction mixture. The methanol may be removed by distillation. The pH of the solution is adjusted to the isoelectric point of the product (i.e., homocysteine). Ethanol may be added such that the product precipitates. The solid may be filtered and dried.

Approximately 2 equivalents of sodium methoxide in methanol and about 2 equivalents of dimethyl carbonate may be added to a reactor. The homocysteine product (see above) may be added and the reaction mixture is heated to reflux for 3 hr. Water and HCl may be added to consume the excess reagents. The solution may be cooled, wherein the product (methionine) precipitates and may be isolated by filtration.

Example 3

Synthesis of Methionine from 4-Bromo-2-Aminobutanoic Acid Hydrobromide

4-Bromo-2-aminobutanoic acid hydrobromide (1 eq.) was treated with sodium methane thiolate (3.2 eq.) in DMSO (25 eq.) at 80° C. for 1 hour. Methionine (82% yield) and homoserine (2.6% yield) were obtained.

Example 4

Synthesis of Methionine from Methyl-2-Amino-4-Chlorobutyrate

Methyl-2-amino-4-chlorobutyrate was treated with 2.2 or 3.2 equivalents of sodium methane thiolate in DMSO at 80° C. for one hour. These solutions were diluted and the pH was adjusted to approximately 3. This was done to protect the methyl ester from hydrolysis during the derivatization process. The analytical results from this experiment are shown in Table 1. The yields are based on conversion of the chloromethylester. Higher methionine yields were achieved when 3.2 equivalents of NaSMe were used.

TABLE 1

| Ratio of DMSO to chloroester | Temp. (° C.) | Equiv. NaSMe | % Met | % Hser |
|---|---|---|---|---|
| 25 | 80 | 2.2 | 55.57 | 0.78 |
| 25 | 80 | 2.2 | 57.29 | 0.61 |
| 25 | 80 | 2.2 | 58.02 | 0.49 |
| 25 | 80 | 3.2 | 89.76 | 0.16 |
| 25 | 80 | 3.2 | 91.80 | 0.13 |
| 25 | 80 | 3.2 | 89.80 | 0.30 |

Example 5

Synthesis of Methionine from Methyl-2-Amino-4-Chlorobutyrate

Methyl 2-amino-4-chlorobutyrate hydrochloride (100 mg, 0.53 mmol) and NaSCH3 (112 mg, 1.60 mmol) were mixed together in water (2 mL) and stirred at room temperature for 2 hours. HPLC analysis indicated equal amounts of methionine and homoserine.

Example 6

Synthesis of Methionine from Methyl-2-Amino-4-Chlorobutyrate

Methyl 2-amino-4-chlorobutyrate hydrochloride (100 mg, 0.53 mmol) and NaSCH3 (78 mg, 1.12 mmol) were mixed together in methanol (2 mL) and heated to 65° C. for 2 hours. HPLC analysis indicated equal amounts of methionine and methionine methyl ester.

Example 7

Synthesis of Methionine from Cysteine

Methanol (11.8 mL) was added to a 100-mL 3-neck flask fitted with a magnetic stirrer, thermocouple, reflux condenser and septum. Anhydrous sodium methoxide (4.04 g, 0.074 mol, 2 eq) was added portionwise over 10 minutes at <35° C. to make a 30% solution. To this was added over 3 minutes, 6.69 g (0.074 mol, 2 eq) of dimethylcarbonate. The mixture initially exothermed from 24° C. to 26° C. then endothermed to 21° C. and was slightly hazy. To this solution was added over 7 minutes 5.0 g (0.037 mol, 1 eq) of DL-homocysteine. The solution exothermed to 32° C. and became a little more hazy and slightly pink. The mixture was heated to reflux (pot 65.5° C.). Additional methanol (27 mL) was added to facilitate stirring. The slurry was allowed to reflux overnight. The reaction mixture was worked up by cooling to 8° C., adding 15.4 g water at <19° C. (solids dissolved), and neutralizing to pH 6-7 with concentrated HCl (6.3 g, 0.062 mol, 0.84 eq). Outgassing of $CO_2$ occurred between pH 14 and 9, and solids precipitated The mixture was stripped at full vacuum and 40° C. to yield a tacky white residue, 17.0 g net. This was transferred back to the reactor with 35.3 g acetic acid. The slurry was heated to 91° C. under nitrogen for 1 hour, then hot-filtered and washed on a filter with 2.2 g hot acetic acid. The acetic acid filtrate was stripped at full vacuum and 40° C. to a tacky white residue, (net wt 14.2 g). To the residue was added 35.5 mL methanol, stirred at room temperature for 30 minutes, filtered, washed with 12 mL methanol, and dried under nitrogen over the weekend. The dried material was washed one more time with 25 mL methanol, filtered, dried under nitrogen to a final weight of 3.455 g (63% crude yield). The crude product was characterized with $^1H$, $^{13}C$ NMR and FTIR and was consistent with authentic methionine. Elemental analysis was low, indicating presence of inorganic material (NaCl assumed), and calculated for $C_5H_{11}NO_2S$:0.8NaCl as: C, 30.65; H, 5.66; N, 7.15, S 16.36. Found: C, 30.69; H, 5.55; N, 7.17, S, 16.11. Assay by elemental analysis: 76.1% methionine, 23.9% NaCl. Net overall yield of 100% assay: 48%.

What is claimed is:

1. A process for preparing a compound comprising Formula (III) or a pharmaceutically acceptable salt thereof, the process comprising:
   a) contacting a compound comprising Formula (I) with a compound comprising X and a proton donor to form a salt of the compound comprising Formula (II), wherein the compound comprising X and the proton donor are different compounds; and
   b) contacting the compound comprising Formula (II) with a compound comprising MeZ to form the compound comprising Formula (III) or the pharmaceutically acceptable salt thereof:

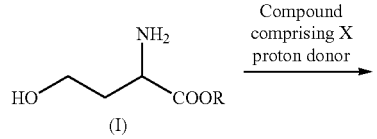

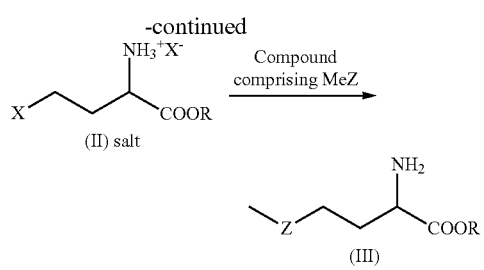

wherein:
   the compound comprising MeZ is sodium methanethiolate;
   R is hydrogen; and
   the compound comprising X is HCl; the proton donor is $H_2SO_4$; the molar ratio of the compound comprising Formula (I) to the compound comprising X to the proton donor is about 1:1.1:0.01; step (a) is conducted in the presence of water as a solvent, at a temperature of about 70° C., and at a pressure of about 80 psig; the molar ratio of the compound comprising Formula (II) to sodium methanethiolate is about 1:3; step (b) is conducted in the presence of n-butanol as a solvent; the molar ratio of the solvent to the salt of the compound comprising the salt of Formula (II) is about 10:1; step (b) is conducted at a temperature of about 80° C.; and the compound comprising Formula (III) or its salt has a yield of at least about 90% w/w.

2. The process of claim 1, wherein the compound comprising Formula (III) or the pharmaceutically acceptable salt thereof has an L configuration or a D configuration.

3. A process for preparing a compound comprising Formula (III) or a pharmaceutically acceptable salt thereof, the process comprising:
   a) contacting a compound comprising Formula (I) with i) a compound comprising X and a proton donor and ii) an acyl donor comprising R' to form a compound comprising Formula (IIa), wherein the compound comprising X and the proton donor are different compounds;
   b) contacting the compound comprising Formula (IIa) with a compound comprising MeZ to form a compound comprising Formula (IIIa) or a pharmaceutically acceptable salt thereof; and
   c) contacting the compound comprising Formula (IIIa) or the pharmaceutically acceptable salt thereof with a deacylating agent to form the compound comprising Formula (III) or the pharmaceutically acceptable salt thereof:

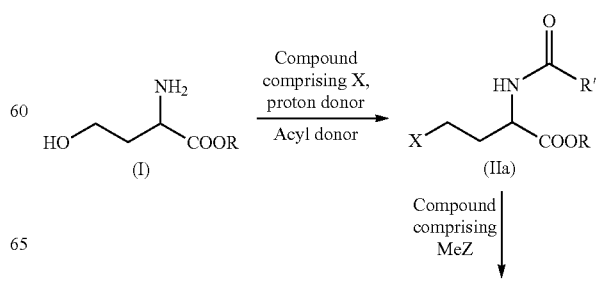

-continued

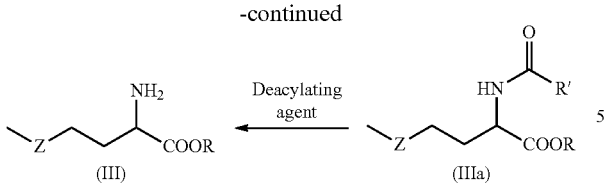

wherein:
the compound comprising MeZ is sodium methanethiolate;
R is hydrogen;
R' is chosen from hydrogen, hydrocarbyl, and substituted hydrocarbyl;
and
the compound comprising X is HCl; the proton donor is $H_2SO_4$; the molar ratio of the compound comprising Formula (I) to the compound comprising X to the proton donor is about 1:1.1:0.01; the molar ratio of the compound comprising Formula (IIa) to sodium methanethiolate is about 1:3; and the compound comprising Formula (III) or its salt has a yield of at least about 90% w/w.

4. The process of claim 3, wherein the acyl donor is chosen from an acyl halide and an acid anhydride.

5. The process of claim 3, wherein contact with the acyl donor is conducted in the presence of a catalyst.

6. The process of claim 3, wherein step (a) is conducted in the presence of a protic solvent chosen from water, formic acid, acetic acid, a C1-C4 alcohol, propylene glycol, and combinations thereof; and the molar ratio of the protic solvent to the compound comprising Formula (I) is from about 0.1:1 to about 20:1.

7. The process of claim 3, wherein step (a) is conducted at a temperature of about 20° C. to about 200° C. and at a pressure of about 0 psig to about 100 psig.

8. The process of claim 3, wherein step (b) is conducted at a temperature from about 20° C. to about 200° C., at ambient pressure, and under an inert gas chosen from nitrogen and argon.

9. The process of claim 3, wherein the deacylating agent is chosen from a proton donor and an acylase.

10. The process of claim 3, wherein step (c) is conducted at a temperature from about 20° C. to about 100° C. and at ambient pressure and atmosphere.

11. The process of claim 3, wherein the compound comprising Formula (III) or the pharmaceutically acceptable salt thereof has an L configuration or a D configuration.

12. A process for preparing a compound Formula (III) or a pharmaceutically acceptable salt thereof, the process comprising contacting a compound comprising Formula (II) or a pharmaceutically acceptable salt thereof with a compound comprising MeZ to form the compound comprising Formula (III) or the pharmaceutically acceptable salt thereof:

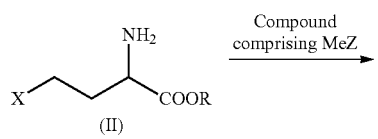

-continued

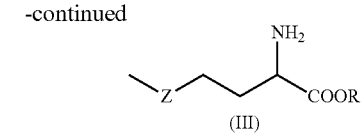

wherein:
the compound comprising MeZ is chosen from an alkali metal methanethiolate, an alkali metal methaneselenoate, and methyl selenol;
Me is methyl;
R is chosen from hydrogen, hydrocarbyl, and substituted hydrocarbyl;
X is a leaving group; and
Z is sulfur or selenium; and
wherein the molar ratio of the compound comprising Formula (II) to the compound comprising MeZ is about 3.2.

13. The process of claim 12, wherein X is chosen from halogen, mesylate, tosylate, brosylate, and nosylate.

14. The process of claim 12, wherein the reaction is conducted in the presence of a solvent chosen from an aprotic solvent, a protic solvent, and combinations thereof; and wherein the molar ratio of the solvent to the compound comprising Formula (II) is from about 1:1 to about 50:1.

15. The process of claim 14, wherein the aprotic solvent is chosen from acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, and combinations thereof; and the protic solvent is chosen from water, a C1-C4 alcohol, propylene glycol, and combinations thereof.

16. The process of claim 12, wherein the reaction is conducted in the presence of a solvent chosen from an aprotic solvent, a protic solvent, an organic solvent, and combinations thereof; and wherein the molar ratio of the solvent to the compound comprising Formula (II) is from about 1:1 to about 50:1.

17. The process of claim 12, wherein the reaction is conducted at a temperature from about 20° C. to about 200° C., at ambient pressure, and under an inert gas chosen from nitrogen and argon.

18. The process of claim 12, wherein the compound comprising Formula (III) or the pharmaceutically acceptable salt thereof has an L configuration or a D configuration.

19. The process of claim 12, wherein R is hydrogen; the compound comprising MeZ is sodium methanethiolate; the reaction is conducted in the presence of n-butanol as a solvent; the molar ratio of the solvent to the compound comprising Formula (II) is about 10:1; and the reaction is conducted at a temperature of about 80° C.

20. A process for preparing a compound Formula (III) or a pharmaceutically acceptable salt thereof, the process comprising:
a) contacting a compound comprising Formula (IIa) with a compound comprising MeZ to form a compound comprising Formula (IIIa) or a pharmaceutically acceptable salt thereof; and
b) contacting the compound comprising Formula (IIIa) or the pharmaceutically acceptable salt thereof with a deacylating agent to form the compound comprising Formula (III) or the pharmaceutically acceptable salt thereof:

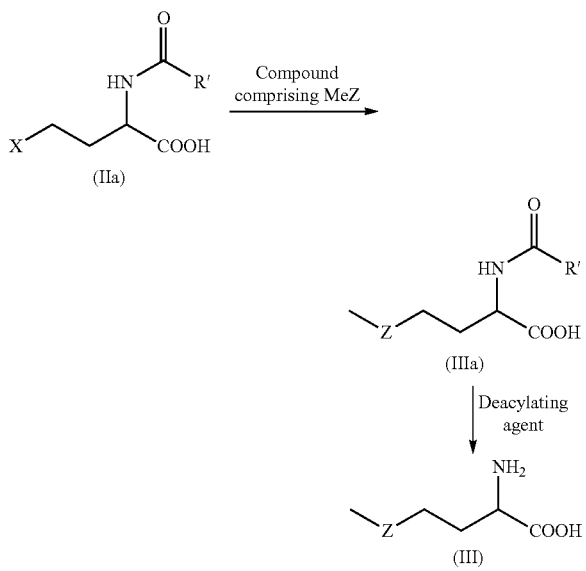

wherein:
- the compound comprising MeZ is chosen from an alkali metal methanethiolate, an alkali metal methaneselenoate, and methyl selenol;
- Me is methyl;
- R is chosen from hydrogen, hydrocarbyl, and substituted hydrocarbyl;
- R' is chosen from hydrogen, hydrocarbyl, and substituted hydrocarbyl;
- X is a leaving group; and
- Z is sulfur or selenium; and wherein the molar ratio of the compound comprising Formula (IIa) to the compound comprising MeZ is about 3.2.

21. The process of claim 20, wherein X is chosen from halogen, mesylate, tosylate, brosylate, and nosylate.

22. The process of claim 20, wherein step (a) is conducted in the presence of a solvent chosen from an aprotic solvent, a protic solvent, and combinations thereof; and wherein the molar ratio of the solvent to the compound comprising Formula (IIa) is from about 1:1 to about 50:1.

23. The process of claim 22, wherein the aprotic solvent is chosen from acetonitrile, dimethyl sulfoxide, N,N-dimethylformamide, N,N-dimethylacetamide, N-methyl-2-pyrrolidinone, formamide, ionic liquids, tetrahydrofuran, 2-methyl tetrahydrofuran, and combinations thereof; and the protic solvent is chosen from water, a C1-C4 alcohol, propylene glycol, and combinations thereof.

24. The process of claim 20, wherein step (a) is conducted in the presence of a solvent chosen from an aprotic solvent, a protic solvent, an organic solvent, and combinations thereof; and wherein the molar ratio of the solvent to the compound comprising Formula (IIa) is from about 1:1 to about 50:1.

25. The process of claim 20, wherein step (a) is conducted at a temperature from about 20° C. to about 200° C., at ambient pressure, and under an inert gas chosen from nitrogen and argon.

26. The process of claim 20, wherein the deacylating agent is chosen from a proton donor and an acylase.

27. The process of claim 20, wherein step (b) is conducted at a temperature from about 20° C. to about 100° C. and at ambient pressure and atmosphere.

28. The process of claim 20, wherein the compound comprising Formula (III) or the pharmaceutically acceptable salt thereof has an L configuration or a D configuration.

* * * * *